United States Patent
Mashat et al.

(10) Patent No.: US 8,993,008 B1
(45) Date of Patent: Mar. 31, 2015

(54) HERBAL COMPOSITION FOR TREATING DIABETES

(71) Applicant: UMM Al-Qura University, Makkah (SA)

(72) Inventors: Bassam Hussain Mashat, Makkah (SA); Ahmed Mohamed Ihab, Makkah (SA)

(73) Assignee: UMM Al-Qura University, Makkah (SA)

( * ) Notice: Subject to any disclaimer, the term of this patent is extended or adjusted under 35 U.S.C. 154(b) by 0 days.

(21) Appl. No.: 14/108,276

(22) Filed: Dec. 16, 2013

(51) Int. Cl.
| | |
|---|---|
| *A01N 65/00* | (2009.01) |
| *A61K 36/54* | (2006.01) |
| *A61K 36/258* | (2006.01) |
| *A61K 36/33* | (2006.01) |
| *A61K 36/42* | (2006.01) |
| *A61K 36/45* | (2006.01) |
| *A61K 36/48* | (2006.01) |
| *A61K 36/51* | (2006.01) |
| *A61K 36/88* | (2006.01) |

(52) U.S. Cl.
CPC .............. *A61K 36/54* (2013.01); *A61K 36/258* (2013.01); *A61K 36/33* (2013.01); *A61K 36/42* (2013.01); *A61K 36/45* (2013.01); *A61K 36/48* (2013.01); *A61K 36/51* (2013.01); *A61K 36/88* (2013.01)
USPC ....................................................... 424/725

(58) Field of Classification Search
None
See application file for complete search history.

(56) References Cited

U.S. PATENT DOCUMENTS

| 5,741,491 A | 4/1998 | Jones |
| 2005/0129617 A1 | 6/2005 | Tan et al. |
| 2011/0117226 A1 | 5/2011 | Terruzzi et al. |
| 2011/0236488 A1 | 9/2011 | Krishnan |

FOREIGN PATENT DOCUMENTS

WO    WO 2009/018648 A1    2/2009

OTHER PUBLICATIONS

WallBetX® GlucoRegulator; printed from http://naturalfactors.com/caen/products/detail/2716/wellbetx-glucoregulator; 6 pages, printed on Oct. 16, 2013.

*Primary Examiner* — Michael Meller
(74) *Attorney, Agent, or Firm* — Richard C. Litman

(57) ABSTRACT

The herbal composition for treating diabetes is a mixture of medicinal herbs, including gymnema (*Gymnema sylvestre*), bilberry (*Vaccinium myrtillus*), Asian ginseng (*Panax ginseng*), fenugreek (*Trigonella foennum-graecum*), marshmallow (*Althaea officinalis*), "true cinnamon" (also known as "Ceylon cinnamon" or "Sri Lanka cinnamon") (*Cinnamomum verum*), bitter melon (also known as "bitter gourd") (*Momordica charantia*), autumn crocus (also known as "meadow saffron") (*Colchicum autumnale*), bay laurel (*Laurus nobilis*), colocynth (*Citrullus colocynthis*) and prickly pear (also known as "cactus pear") (*Opuntia ficus-indica*). Preferably, the herbal components of the above composition are dried, ground and packaged in a teabag or the like, allowing the composition to be delivered to the patient as an aqueous extract, similar to a conventional herbal tea. Preferably, about 5 grams of the composition are contained in the teabag, which is steeped in about 150 mL of boiling water for between about three minutes and about five minutes.

1 Claim, No Drawings

HERBAL COMPOSITION FOR TREATING DIABETES

BACKGROUND OF THE INVENTION

1. Field of the Invention

The present invention relates to treatment of type I diabetes, and particularly to an herbal composition for enhancing insulin excretion and controlling blood glucose levels in patients with type I diabetes.

2. Description of the Related Art

Diabetes mellitus type 1 (also known as "type I diabetes") is a form of diabetes mellitus that results from autoimmune destruction of insulin-producing beta cells of the pancreas. The subsequent lack of insulin leads to increased blood and urine glucose. The classical symptoms are polyuria (frequent urination), polydipsia (increased thirst), polyphagia (increased hunger), and weight loss. Untreated, type I diabetes is ultimately fatal, but the disease is commonly controlled with supplemental insulin. Insulin is most commonly administered by injection at periodic intervals several times per day, although other options, such as insulin pumps, exist. Transplantation, both of the entire pancreas and pancreatic islet cells, is a possible cure in some cases. Given the reliance of the patient on insulin injections, or through the invasive procedures noted above, it would obviously be desirable to be able to enhance the patient's natural excretion of insulin and control blood glucose levels without injections, pumps or surgical procedures.

Thus, an herbal composition for treating diabetes solving the aforementioned problems is desired.

SUMMARY OF THE INVENTION

The herbal composition for treating diabetes is a mixture of medicinal herbs, including gymnema (*Gymnema sylvestre*), bilberry (*Vaccinium myrtillus*), Asian ginseng (*Panax ginseng*), fenugreek (*Trigonella foenum-graecum*), marshmallow (*Althaea officinalis*), "true cinnamon" (also known as "Ceylon cinnamon" or "Sri Lanka cinnamon") (*Cinnamomum verum*), bitter melon (also known as "bitter gourd") (*Momordica charantia*), autumn crocus (also known as "meadow saffron") (*Colchicum autumnale*), bay laurel (*Laurus nobilis*), colocynth (*Citrullus colocynthis*) and prickly pear (also known as "cactus pear") (*Opuntia ficus-indica*). Preferably, the herbal components of the above composition are dried, ground, and packaged in a teabag or the like, allowing the composition to be delivered to the patient as an aqueous extract of the active ingredients in the herbs, similar to a conventional herbal tea. Preferably, about 5 grams of the composition are contained in the teabag, which is steeped in about 150 mL of boiling water for between about three minutes and about five minutes.

These and other features of the present invention will become readily apparent upon further review of the following specification.

DETAILED DESCRIPTION OF THE PREFERRED EMBODIMENTS

The herbal composition for treating diabetes is a mixture of medicinal herbs, including about 5 wt % gymnema (*Gymnema sylvestre*), about 2 wt % bilberry (*Vaccinium myrtillus*), about 11 wt % Asian ginseng (*Panax ginseng*), about 20 wt % fenugreek (*Trigonella foenum-graecum*), about 5 wt % marshmallow (*Althaea officinalis*), about 20 wt % "true cinnamon" (also known as "Ceylon cinnamon" or "Sri Lanka cinnamon") (*Cinnamomum verum*), about 10 wt % bitter melon (also known as "bitter gourd") (*Momordica charantia*), about 10 wt % autumn crocus (also known as "meadow saffron") (*Colchicum autumnale*), about 10 wt % bay laurel (*Laurus nobilis*), about 2 wt % colocynth (*Citrullus colocynthis*), and about 5 wt % prickly pear (also known as "cactus pear") (*Opuntia ficus-indica*).

Preferably, the herbal components of the above composition are dried, ground and packaged in a teabag or the like, allowing the composition to be delivered to the patient as an aqueous extract of the active ingredients in the herbs, similar to a conventional herbal tea. Preferably, about 5 grams of the composition are contained in the teabag, which is steeped in about 150 mL of boiling water for between about three minutes and about five minutes. The composition aids the patient suffering from type I diabetes in stimulating insulin excretion and controlling blood glucose levels. The preferred dosage is delivered as described above, with the patient using between one and two teabags full of the herbal composition per day.

The various ingredients have the following effects. Gymnema is an herb that increases circulating insulin and C-peptide, which reduce fasting and post-prandial glucose. Gymnema sylvestre extract stimulates insulin secretion in human islets, both in vitro and in vivo. Bilberry lowers blood sugar levels. Asian ginseng reduces post-prandial blood sugar. Fenugreek reduces glucose levels during meals. Marshmallow lowers blood glucose levels. Cinnamon has an antioxidant effect and has the potential to maintain healthy blood glucose sugar levels. Bitter gourd has the ability to enhance cell uptake of glucose, to promote insulin release, and to potentiate the effect of insulin. Colchicine decreases insulin secretion in response to glucose and maintains glucose levels, so that colchicine inhibits glucose-induced insulin secretion and deteriorates glucose tolerance in humans. Laurel reduces serum glucose levels. Colocynth is an herb believed to have anti-diabetic effects, particularly in preserving or restoring pancreatic β-cell mass and stimulating insulin secretion. Prickly pear is an insoluble fiber that slows down how long it takes the sugar to be released into the blood stream.

While the foregoing summarizes the effects of the ingredients when taken individually, the present herbal composition provides a balanced approach to the management of Type I diabetes. It is believed that in some cases the ingredients are complementary to each other so that one exerts an effect when the other does not, and in some cases the ingredients exert a synergistic effect on each other so that one ingredient is more effective than it would be in the absence of the other.

It is to be understood that the present invention is not limited to the embodiments described above, but encompasses any and all embodiments within the scope of the following claims.

We claim:

1. A method of treating diabetes in a human in need thereof consisting essentially of administering to said human therapeutically effective amounts of gymnema extract, bilberry extract, Asian ginseng extract, fenugreek extract, marshmallow extract, Ceylon cinnamon extract, bitter melon extract, autumn crocus extract, bay laurel extract, colocynth extract and prickly pear extract to effectively treat the diabetes in said human.

* * * * *